United States Patent [19]

Seitz et al.

[11] Patent Number: 5,801,263
[45] Date of Patent: Sep. 1, 1998

[54] PROCESS FOR PREPARING TERTIARY PHOSPHINES CONTAINING PHOSPHINATE OR PHOSPHONATE GROUPS, AND NOVEL TERTIARY PHOSPHINES CONTAINING PHOSPHINATE GROUPS

[75] Inventors: Thomas Seitz, Heddesheim; Steffen Haber, Königstein; Hans-Jerg Kleiner, Kronberg, all of Germany

[73] Assignee: Hoechst Aktiengesellschaft, Germany

[21] Appl. No.: 857,755

[22] Filed: May 15, 1997

[30] Foreign Application Priority Data

May 17, 1996 [DE] Germany .................. 196 20 023.7

[51] Int. Cl.$^6$ .................. C07F 9/30; C07F 9/50
[52] U.S. Cl. .................. 558/155; 568/12; 568/17; 562/20; 558/155
[58] Field of Search .................. 568/12, 17; 562/20; 558/155

[56] References Cited

U.S. PATENT DOCUMENTS 3,992,273  11/1976  Miles et al. .................. 204/158
5,516,944  5/1996  Broger .................. 568/13

FOREIGN PATENT DOCUMENTS 0470795  2/1992  European Pat. Off. .

OTHER PUBLICATIONS

CA:123:256859, abst of "The first examples of an aryl ring substituted by both phosphine and phosphonate moieties", Schull, J Chem Soc, Chem Commun., (15) pp. 1487–1488, 1995.

Baldwin et al: "Application of the Hammett equation to Organophosphorus–substituted phosphinic and benzoic acids", J. Org. Chem.: vol. 32 (7); pp. 2176–2180, American Potash and Chem. Corp.; Whittier; CA XP002039488 (1967).

Schull et al: "The first examples of an aryl ring substituted by both phosphine and phosphonate moieties: synthesis and characterization of the new highly water–soluble phosphine ligand . . . ". J. Chem. Soc., Chem. Commun.; (15); pp. 1487–1488, George Washington University; Dep. Chem.; Washington.; 20052: DC XP002039489 (1995).

Phosphorus, Sulfur Silicon Relat. Elem. 96: vol. 117.; pp. 287–292, Germany. "Aromatic phosphonate–phosphines". (Jun. 10, 1996).

Baldwin, et al. "Application of the Hammett Equation to Organophosphorus–Substituted Phosphinic and Benzoic Acids", J. Org. Chem 32: pp. 2176–2180 (1967).

Xu, et al. "Palladium–Catalysed Synthesis of Functionalised Alkyl Alkylarylphosphinates", Synthesis 9: pp. 778–781 (1984).

Cornils, et al. "Aqueous catalysts for organic reactions", Chemtech Jan: pp. 33–38 (1995).

Schull, et al. "The First Examples of an Aryl Ring Substituted by Both Phosphine and Phosphonate Moieties: Synthesis and Characterization of the New Highly Water–Soluble Phosphine Ligand $Na_2[Ph_2P(C_6H_4-p-PO_3)]$–$1.5H_2O$ and Platinum(II) Complexes", J. Chem. Soc., Chem. Commun.: pp. 1487–1488 (1995).

Primary Examiner—Gary Geist
Assistant Examiner—Jean F. Vollano
Attorney, Agent, or Firm—Connolly & Hutz

[57] ABSTRACT

Tertiary phosphines of the formula (I)

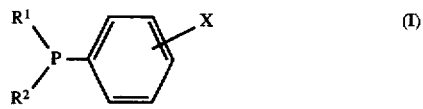

in which X is a phosphinate or phosphonate group, are prepared by a palladium-catalyzed coupling of p-, m- or o-bromofluorobenzenes with alkyl akylphosphonous acid ester or alkyl alkylphosphite ester and reacting the resulting alkyl fluorophenylphosphinates or alkyl fluorophenylphosphonates with a metal phosphide.

6 Claims, No Drawings

PROCESS FOR PREPARING TERTIARY PHOSPHINES CONTAINING PHOSPHINATE OR PHOSPHONATE GROUPS, AND NOVEL TERTIARY PHOSPHINES CONTAINING PHOSPHINATE GROUPS

DESCRIPTION

The present invention is in the field of organic phosphorus chemistry. The invention relates to the preparation of tertiary phosphines bearing phosphinate or phosphonate groups by nucleophilic substitution of fluoroarylphosphonates or fluoroarylphosphinates with secondary phosphides. The novel phosphinates or phosphonates accessible by this route are used as a constituent of catalyst systems.

Complex compounds which contain, as central atom, a metal of the 8th subgroups of the Periodic Table of the Elements and, as ligands, P(III) compounds, namely phosphines or phosphites and, in addition, if appropriate other groups capable of complex formation, are in recent years increasingly being used as catalysts for syntheses in organic chemistry. Instead of in the homogeneous phase, the reactions can also be carried out in heterogeneous multiphasic reaction systems. An advantage of this process variant is the simple and gentle separation of the catalyst dissolved in the water from the water-insoluble reaction product.

Two-phase processes have also proved very useful on the industrial scale, for which reason it is a worthwhile object to provide novel compounds from the group of the water-soluble phosphines, in order to supplement and expand possible applications.

In J. Chem. Soc., Chem. Commun. 1995, 1487–1488, triphenylphosphine monophosphonates are prepared by lithiation of diphenylphosphino-p-bromobenzene. By means of this process and the process described in J. Org. Chem. 32, 1967, 2176–2180, whose key step in each case is the lithiation of para-bromotriphenylphosphine, the synthesis of the corresponding ortho-isomers is not possible, owing to the inaccessibility of ortho-bromotriphenylphosphine.

The object therefore underlying the present invention was to develop a process for preparing tertiary phosphines by which phosphinate and/or phosphonate groups can be introduced into the para, meta and ortho position to the trivalent phosphorus atom.

This object is achieved by a palladium-catalyzed coupling of bromofluorobenzenes with alkyl alkylphosphonous acid ester or with alkyl alkylphosphite ester and reacting the resulting alkyl fluorophenylphosphinates or alkyl fluorophenylphosphonates with a metal phosphide.

The present invention relates to a process for preparing a tertiary phosphine of the formula (I)

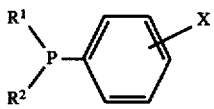

in which

X is a group of the formulae (Ia) or (Ib),

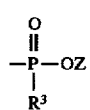

(Ia)

$$\overset{O}{\underset{R^3}{\overset{\|}{-P-OZ}}}$$

(Ib)

$$\overset{O}{\underset{OZ}{\overset{\|}{-P-OZ}}}$$

where

Z is hydrogen, an alkali metal, the stoichiometric equivalent of an alkaline earth metal, an ammonium ion, a mono-, di-, tri- or tetraalkylammonium ion or a radical $R^4$, where $R^4$ is a $C_1$–$C_{30}$-alkyl radical; and $R^3$ is a linear or branched $C_1$–$C_4$-alkyl radical;

$R^1$ and $R^2$ are identical or different and are each a linear, branched or cyclic $C_1$–$C_{30}$-alkyl radical or $C_6$–$C_{10}$-aryl radical which is unsubstituted or mono-substituted to penta-substituted by $C_1$–$C_3$-alkyl radicals, or $R^1$ and $R^2$ together with the trivalent P atom form a dibenzophospholyl of the formula

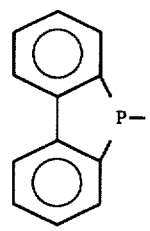

or a 3,4-dimethylphospholyl of the formula

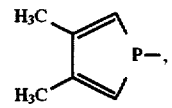

which comprises reacting, in the presence of a phosphine-containing palladium catalyst and a base, a bromofluorobenzene of the formula (V)

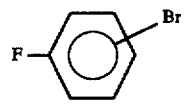

(V)

either with a $(C_1$–$C_4)$-alkyl $(C_1$–$C_4)$-alkylphosphonous acid ester of the formula (IVa) to give a $(C_1$–$C_4)$-alkyl fluorophenylphosphinate of the formula (IIIa)

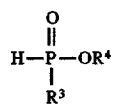

(IVa)

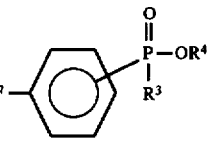

(IIIa)

or with a di-$(C_1$–$C_4)$-alkyl phosphite ester of the formula (IVb) to give a di-$(C_1$–$C_4)$-alkyl fluorophenylphosphonate of the formula (IIIb)

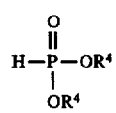

(IVb)

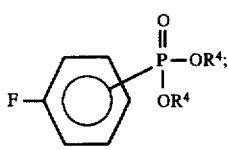

reacting the compound of the formula (IIIa) or the formula (IIIb) with an alkali metal phosphide or alkaline earth metal phosphide of the formula (II)

in which M is an alkali metal or the stoichiometric equivalent of an alkaline earth metal, in a polar aprotic solvent, to give a tertiary phosphinylphosphinate of the formula (Ic) or to give a tertiary phosphinylphosphonate of the formula (Id)

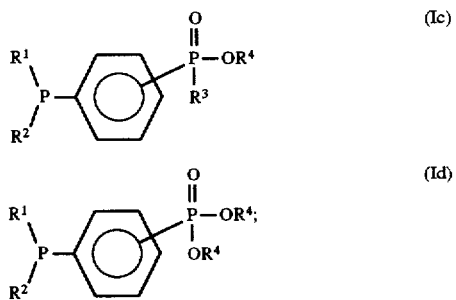

optionally saponifying the tertiary phosphinylphosphinate or the tertiary phosphinylphosphonate, with the salt-like compounds of the formulae (Ia) or (Ib) where Z is alkali metal, the stoichiometric equivalent of an alkaline earth metal, of an ammonium or mono-, di-, tri- or tetraalkylammonium ion being formed; and
optionally adding a mineral acid to the salt-like compounds of the formula (Ia) or (Ib), so that the free acids of the compounds of the formulae (Ia) or (Ib) where Z is hydrogen are formed.

In the compounds of the formulae above, the variables have the following preferred meanings:

Z is hydrogen, $Na^+$, $K^+$, $\frac{1}{2}Mg^{2+}$, $\frac{1}{2}Ca^{2+}$, $NH_4^+$, a mono-, di-, tri or tetra-($C_1$–$C_4$)-alkylammonium or a radical $R^4$ which is preferably $C_1$–$C_6$-alkyl, in particular a $C_4$-alkyl;

$R^3$ is methyl or ethyl;

$R^1$ and $R^2$ are identical and are each a linear or branched $C_1$–$C_6$-alkyl radical, a cyclohexyl radical or a phenyl radical; and M is $Na^+$, $K^+$, $\frac{1}{2}Ca^{2+}$ or $\frac{1}{2}Mg^{2+}$.

The group X in the compounds of the formula (I) and the phosphinate or phosphonate groups in the compounds of the formulae (Ia) to (Id) can be in the ortho, meta or para position to the trivalent phosphorus atom. Correspondingly, in the bromofluorobenzene of the formula (V), the bromine atom can be in the ortho, meta or para position to the fluorine atom.

In the process according to the invention, the bromofluorobenzene is expediently reacted with the alkyl alkylphosphonous acid ester, or dialkyl phosphite ester in a molar ratio of 1:1 to 1:1.5 in an organic solvent. The temperature is 80° to 150° C., preferably 95° to 120° C.

The phosphine-containing palladium catalyst can be synthesized in situ by adding a plurality of equivalents of a phosphine and a palladium compound, with mono- or bis-, alkyl- or arylphosphines being able to be used; preference is given to triphenylphosphine. In the case of the palladium compound used, use is preferably made of palladium(II) salts, e.g. Pd(II) chloride or Pd(II) acetate, or of palladium (O) compounds, e.g. palladium bis(dibenzylideneacetone), which is particpreferred. 0.1 to 4.5 mol %, preferably 0.5 to 2 mol %, of the palladium catalyst are sufficient for the reaction according to the invention. A use of 5 mol % or even 10 mol % of the expensive tetrakis-(triphenylphosphine) palladium, as described in J. Chem. Soc. Perkin Trans. 1 (1995) 1145 or in Synthesis 9, (1984) 778, is not necessary. Suitable organic solvents are dimethylformamide, dimethyl sulfoxide, xylenes or toluene. Suitable bases are, e.g., sodium acetate or potassium acetate, alkali metal carbonates or alkaline earth metal carbonates and trialkylamines. Very particular preference is given to triethylamine, which simultaneously serves as solvent. The reaction times, depending on substrate and reagent, are between 2 and 50 hours.

The nucleophilic substitution of the fluoride in the compounds of the formulae (IIIa) and (IIIb) is carried out using 1 to 1.5 mol equivalents of the alkali metal phosphide or alkaline earth metal phosphide in a polar aprotic solvent at –5° C. to +100° C. Preferably, the reaction takes place in ethers at –5° C. to +50° C., in particular preference is given to tetrahydrofuran as solvent and a temperature of –5° C. to +23° C. Depending on substrate and reagent, the reaction times are between 2 and 72 hours.

The compounds of the formulae (Ic) and (Id) can be purified by crystallization or column chromatography, but this is not absolutely necessary for further reactions.

The ester saponification to give the tertiary phosphinylphosphinate salts or phosphinylphosphonate salts of the formulae (Ia) and (Ib) is preferably performed in a mixture of tetrahydrofuran and 1 to 3 mol equivalents of aqueous base, in particular alkali metal hydroxide solution, under reflux conditions for 3 to 12 hours. By neutralization with aqueous mineral acid, concentration, taking up the residue in organic solvents and separating off the inorganic salts by filtration, after removal of the solvent, the free phosphinic acids or phosphonic acids are obtained.

From the water-insoluble acids, by treating with equimolar amounts of alkali metal hydroxide, alkali metal hydrogen carbonate or alkali metal carbonate in water, the aqueous phosphinate solutions or phosphonate solutions in the desired molarity are obtained.

As an alternative thereto, the corresponding salts of the phosphinic acids or phosphonic acids can also be obtained directly, after alkaline saponification has been performed, by recrystallizing the evaporation residue.

The process according to the invention, in comparison with the process described in U.S. Pat. No. 3,992,273, in which fluoroiodobenzenes are reacted with trialkylphosphonites under UV irradiation to give fluorophenylphosphonous esters, has the advantage that the less expensive bromofluorobenzenes can be used.

The present invention further relates to compounds of the formula (I)

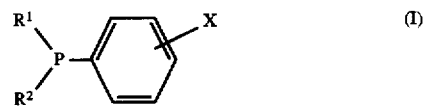

in which

X is a group of the formula (Ia)

in which
Z is hydrogen, an alkali metal, the stoichiometric equivalent of an alkaline earth metal, an ammonium ion, a mono-, di-, tri- or tetraalkylammonium or a radical $R^4$, where $R^4$ is a $C_1$–$C_{30}$-alkyl radical; and
$R^3$ is a linear or branched $C_1$–$C_4$-alkyl radical;
$R^1$ and $R^2$ are identical or different and are each a linear, branched or cyclic $C_1$–$C_{30}$-alkyl radical or $C_6$–$C_{10}$-aryl radical which is unsubstituted or mono-substituted to penta-substituted by $C_1$–$C_3$-alkyl radicals, or $R^1$ and $R^2$ together with the trivalent P atom form a dibenzophospholyl of the formula

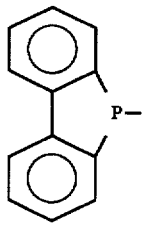

or a 3,4-dimethylphospholyl of the formula

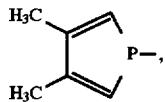

Preference is given to compounds of the formula (I), in which
Z is $H^+$, $Na^+$, $K^+$, $Mg^{2+}/2$, $Ca^{2+}/2$, $NH_4^+$, mono-, di-, tri- or tetra-$(C_1$–$C_4)$-alkylammonium, methyl, ethyl, n-propyl, isopropyl, n-butyl, isobutyl or tert-butyl;
$R^3$ is methyl or ethyl; and
$R^1$ and $R^2$ are each methyl, cyclohexyl or phenyl.
Particularly preferably, $R^4$ is a butyl radical, in particular isobutyl.
The phosphinate group can be in the ortho, meta or para position to the trivalent phosphorus atom. Very particular preference is given to the compounds isobutyl (4-diphenylphosphinophenyl)methylphosphinate, isobutyl (3-diphenylphosphinophenyl)methylphosphinate and isobutyl (2-diphenylphosphinophenyl)methylphosphinate; (4-diphenylphosphinophenyl)methylphosphinic acid, (3-diphenylphosphinophenyl)methylphosphinic acid and (2-diphenylphosphinophenyl)methylphosphinic acid, and the sodium salts of said acids.
In particular the sodium salt of (4-diphenylphosphinophenyl)methylphosphinic acid is distinguished—despite the hydrophobic methyl group and the single negative charge of the anion—surprisingly, by a higher water solubility (590 g/l) both in comparison with the disodium salt of triphenylphosphinemonophosphonate ("Na$_2$TPPMP", 380 g/l at 20° C. [Chemtech, 1995, 33–38]) and with the sodium salt of triphenylphosphinemonosulfonate ("Na[TPPMS]", 80 g/l at 20° C. [J. Chem. Soc. Commun. 1995, 1487–1488]).
The compounds of the formula (I) are suitable as ligands in metal-complex-catalyzed organic reactions. They are particularly suitable as catalyst constituents in transition-metal-complex-catalyzed C—C linking reactions. In particular, they are suitable as ligands in the palladium-catalyzed cross-coupling of arylboronic acids with arylhalides (Suzuki coupling). Thus, in the reaction of 2-chlorobenzonitrile with para-tolueneboronic acid, 2-cyano-4'-methylbiphenyl is obtained in good yields, whereas, in EP-A-0 470 795, the considerably more expensive 2-bromobenzonitrile must be used for this.

EXAMPLE 1

(4-Diphenylphosphinophenyl)methylphosphinic Acid 1.1 Isobutyl 4-fluorophenylmethylphosphinate A mixture of 50.0 g (289 mmol) of 4-bromofluorobenzene, 43.3 g (318 mmol) of isobutyl methanephosphonous acid ester, 43.8 ml (318 mmol) of triethylamine, 1.64 g (0.29 mmol, 1 mol %) of palladium-bis-(dibenzylideneacetone) and 1.50 g (0.58 mmol, 2 mol %) of triphenylphosphine is heated at 100° C. for 20 hours under an inert gas atmosphere. At 23° C., the mixture is filtered off from the resulting ammonium salt and the filtrate is concentrated under reduced pressure. After fractional distillation under reduced pressure, 54.60 g (83% of theory) of isobutyl 4-fluorophenylmethylphosphinate having a boiling point of 83° C./0.08 mbar are obtained.

$^1$H-NMR spectrum (CDCl$_3$): 0.91 (s, 3H, CH$_3$); 0.93 (s, 3H, CH$_3$); 1.68 (d, J$_{PH}$=14.7 Hz, 3H, P—CH$_3$); 1.92 (septet, $^3$J$_{HH}$=6.7 Hz, CH-isobutyl); 3.50 (m, 1H, H$_a$—OCH$_2$); 3.81 (m, 1H, H$_b$—OCH$_2$); 7.18 (mc, 2H, aromatic H); 7.81 (mc, 2H, aromatic H) ppm.

$^{13}$C-NMR spectrum (CDCl$_3$): 15.88 (d, $^1$J$_{PC}$=105.0 Hz, P—CH$_3$), 18.77 (d, $^4$J$_{PC}$=3.8 Hz, 2CH$_3$); 29.16 (d, $^3$J$_{PC}$=7.8 Hz, d, CH-isobutyl); 70.41 (d, $^2$J$_{PC}$=6.0 Hz, O—CH$_2$); 115.7–167.6 (aromatic C) ppm.

$^{31}$P-NMR spectrum (CDCl$_3$): 41.2 ppm.

$^{19}$F-NMR spectrum (CDCl$_3$): –106.9 (m) ppm.

1.2 Isobutyl (4-diphenylphosphinophenyl) methylphosphinate 200 ml (100 mmol) of potassium diphenylphosphide solution in THF (manufacturer: Aldrich) are added dropwise at –5° C. to a solution of 21.90 g (95 mmol) of isobutyl 4-fluorophenylmethylphosphinate in 150 ml of THF. After stirring for 20 hours at 23° C., the mixture is hydrolyzed by adding 250 ml of degassed water and stirring for 15 min. After extraction with ethyl acetate, drying the organic phase over Na$_2$SO$_4$, concentrating on a rotary evaporator and drying under reduced pressure, 37.0 g of isobutyl (4-diphenylphosphinophenyl)methylphosphinate are obtained in the form of a yellow oil.

$^1$H-NMR spectrum (CD$_2$Cl$_2$): 0.89 (d, J$_{HH}$=6.7 Hz, 3H, CH$_3$); 0.90 (d, J$_{HH}$=6.7 Hz, 3H, CH$_3$); 1.65 (d, J$_{PH}$=14.6 Hz, 3H, P—CH$_3$); 1.90 (septet, J$_{HH}$=6.7 Hz, CH-isobutyl); 3.51 (m, 1H, H$_a$—OCH$_2$); 3.78 (m, 1H, H$_b$—OCH$_2$); 7.13–7.88 (14H, aromatic H) ppm.

$^{13}$C-NMR spectrum (CD$_2$Cl$_2$): 16.87 (d, $^1$J$_{PC}$=102.7 Hz, P—CH$_3$), 18.69 (d, $^4$J$_{PC}$=3.0 Hz, 2 CH$_3$); 29.11 (d, $^3$J$_{PC}$=6.8 Hz, d, CH-isobutyl); 70.39 (d, $^2$J$_{PC}$=6.6 Hz, O—CH$_2$); 128.60–136.1 (aromatic C) ppm.

$^{31}$P-NMR spectrum (CD$_2$Cl$_2$): 42.5 (phosphinate P); –4.1 (phosphine P) ppm.

1.3 (4-Diphenylphosphinophenyl)methylphosphinic acid 8.70 g (217.5 mmol) of NaOH in 40 ml of water are added dropwise at 23° C. to a solution of 34.52 g (87 mmol) of isobutyl (4-diphenylphosphinophenyl)methylphosphinate in 50 ml of THF. After refluxing for 6 hours, 18.1 ml (218 mmol) of concentrated hydrochloric acid are added dropwise at 23° C., the mixture is stirred for 10 min at 23° C. and evaporated to dryness on a rotary evaporator. The residue is taken up in methylene chloride and the solution is dried over $Na_2SO_4$ and completely evaporated. After drying under reduced pressure, 28.3 g of (4-diphenylphosphinophenyl) methylphosphinic acid (90% of theory) are obtained in the form of a pale yellow solid having an m.p. of 40° C.

$^1$H-NMR spectrum ($CDCl_3$): 1.07 (d, $J_{PH}$=14.2 Hz, 3 Hz, P—$CH_3$); 7.03–7.22 (14 H, aromatic H) ppm.

$^{13}$C-NMR spectrum ($CDCl_3$): 18.04 (d, $^1J_{PC}$=99.2 Hz, P—$CH_3$); 128.48–140.45 (aromatic C)

$^{31}$P-NMR spectrum ($CDCl_3$): 26.7 (phosphinic acid P); −11.5 (phosphine P) ppm. EI mass spectrum: [M$^+$]=340

1.4 Sodium (4-diphenylphosphinophenyl) methylphosphinate 100 ml of a 3.7% strength by weight sodium hydrogen carbonate solution (44.1 mmol $NaHCO_3$) are added to 15.0 g (44.1 mmol) of (4-diphenylphosphinophenyl) methylphosphinic acid and the mixture stirred at room temperature until $CO_2$ formation has ended. The aqueous solution is completely evaporated and dried under reduced pressure. 15.6 g (97% of theory) of sodium (4-diphenylphosphinophenyl)methylphosphinate are obtained. Solubility in water: 590 g/l

EXAMPLE 2

(3-Diphenylphosphinophenyl)methylphosphinic Acid 2.1 Isobutyl 3-fluorophenylmethylphosphinate In a similar procedure to Example 1.1, a batch of 76.30 g (436 mmol) of 3-bromofluorobenzene, 65.29 g (480 mmol) of isobutyl methanephosphonous acid ester, 66.4 ml (480 mmol) of triethylamine, 2.50 g (1 mol %) of palladium bis(dibenzylideneacetone) and 2.28 g (2 mol %) of triphenylphosphine gives, after 17 hours at 100° C., 89.30 g (89% of theory) of isobutyl 3-fluorophenylmethylphosphinate having a boiling point of 96° C./1.30 mbar.

$^1$H-NMR spectrum ($CDCl_3$): 0.91 (s, 3H, $CH_3$); 0.94 (s, 3H,$CH_3$); 1.69 (d, $^2J_{PH}$=15.0 Hz, 3H, P—$CH_3$); 1.94 (septet, J=6.6 Hz, CH-isobutyl); 3.51 (m, 1H, $H_a$—$OCH_2$); 3.82 (m, 1H, $H_b$—$OCH_2$); 7.19–7.61 (4H, aromatic H) ppm.

$^{13}$C-NMR spectrum ($CDCl_3$): 16.70 (d, $^1J_{PC}$=103.5 Hz, P—$CH_3$), 18.73 (s, $CH_3$); 18.77 (s, $CH_3$); 29.16 (d, $^3J_{PC}$=7.5 Hz, CH-isobutyl); 70.58 (d, $^2J_{PC}$=5.5 Hz, O—$CH_2$); 117.89–164.30 (aromatic C) ppm.

$^{31}$P-NMR spectrum ($CDCl_3$): 40.9 (d, $J_{FP}$=6.0 Hz) ppm.

$^{19}$F-NMR spectrum ($CDCl_3$): −111.7 (m) ppm.

2.2 Isobutyl (3-diphenylphosphinophenyl) methylphosphinate 36.5 ml (18.3 mmol) of potassium diphenylphosphide solution in THF (manufacturer: Aldrich) are added dropwise at −5° C. to a solution of 4.00 g (17.4 mmol) of isobutyl 3-fluorophenylmethylphosphinate in 20.0 ml of THF. After stirring for 48 hours at 23° C., the mixture is hydrolyzed by adding 20 ml of degassed water and stirring for 15 min. After extraction with ethyl acetate, drying the organic phase over $Na_2SO_4$, concentration and drying under reduced pressure, 5.60 g of isobutyl (3-diphenylphosphinophenyl) methylphosphinate are obtained in the form of a yellow oil.

$^1$H-NMR spectrum ($CDCl_3$): 0.83 (d, $J_{HH}$=6.5 Hz, 3H, $CH_3$); 0.85 (d, $J_{HH}$=6.5 Hz, 3H, $CH_3$); 1.61 (d, $J_{PH}$=14.3 Hz, 3H, P—$CH_3$); 1.81 (septet, $J_{HH}$=6.6 Hz, CH-isobutyl); 3.41 (m,1H, $H_a$—$OCH_2$); 3.74 (m, 1H, $H_b$—$OCH_2$); 7.26–7.84 (4H, aromatic H) ppm.

$^{13}$C-NMR spectrum ($CDCl_3$): 15.67 (d, $^1J_{PC}$=102.6 Hz, P—$CH_3$), 18.69 (d, $^4J_{PC}$=4.6 Hz, 2 $CH_3$); 29.01 (d, $^3J_{PC}$=6.8 Hz, CH-isobutyl); 70.32 (d, $^2J_{PC}$=6.5 Hz, O—$CH_2$); 128.58–138.83 (aromatic C) ppm.

$^{31}$P-NMR spectrum ($CDCl_3$): 42.5 (phosphinate P); −4.5 (phosphine P) ppm.

2.3 (3-Diphenylphosphinophenyl)methylphosphinic acid 0.50 g (12.6 mmol) of NaOH in 7 ml of water are added dropwise at 23° C. to a solution of 2.50 g (6.3 mmol) of isobutyl (3-diphenylphosphinophenyl)methylphosphinate in 7 ml of THF. After refluxing for 6 hours, 1.04 ml (12.6 mmol) of concentrated hydrochloric acid are added dropwise at 23° C., the mixture is stirred for 10 min at 23° C. and evaporated to dryness under reduced pressure. The residue is substantially dissolved in boiling methanol, filtered hot and crystallized for 22 h at −20° C. 1.02 g of (3-diphenylphosphinophenyl)methylphosphinic acid (60% of theory) are obtained in the form of a colorless solid having an m.p. of 173° C.

$^1$H-NMR spectrum ($D_6$-DMSO): 1.45 (d, $^2J_{PH}$=14.5 Hz, 3H, P—$CH_3$); 7.23–8.08 (14H, aromatic H) ppm.

$^{13}$C-NMR spectrum ($D_6$-DMSO): 16.63 (d, $^1J_{PC}$=99.0 Hz, P—$CH_3$), 128.59–137.29 (aromatic C).

$^{31}$P-NMR spectrum ($D_6$-DMSO): 34.1 (phosphinic acid P); −5.7 (phosphine P) ppm.

EXAMPLE 3

(2-Diphenylphosphinophenyl)methylphosphinic Acid 3.1 Isobutyl 2-fluorophenylmethylphosphinate In a similar manner to Example 1.1, a batch of 100.00 g (578 mmol) of 2-bromofluorobenzene, 86.60 g (636 mmol) of isobutyl methanephosphonous acid ester, 88.1 ml (636 mmol) of triethylamine, 3.28 g (1 mol %) of palladium bis(dibenzylideneacetone) and 3.00 g (2 mol %) of triphenylphosphine, after 48 hours at 100° C., gives 96.30 g (73% of theory) of isobutyl 2-fluorophenylmethylphosphinate having a boiling point of 93° C./1.40 mbar.

$^1$H-NMR spectrum ($CDCl_3$): 0.89 (s, 3H, $CH_3$); 0.91 (s, 3H, $CH_3$); 1.79 (d, $^2J_{PH}$=15.6 Hz, 3H, P—$CH_3$); 1.90 (septet, J=6.7 Hz, CH-isobutyl); 3.48 (m, 1H, $H_a$—$OCH_2$); 3.78 (m, 1H, $H_b$—$OCH_2$); 7.13 (mc, 1H, aromatic H); 7.29 (mc, 1H, aromatic H); 7.56 (mc, 1H, aromatic H); 7.96 (mc, 1H, aromatic H) ppm.

$^{13}$C-NMR spectrum ($CDCl_3$): 16.00 (dd, $^1J_{PC}$=105.0 Hz, $^4J_{FC}$=3.0 Hz, P—$CH_3$), 18.67 (s, 2 $CH_3$); 29.07 (d, $^3J_{PC}$=6.5 Hz, d, CH-isobutyl); 70.73 (d, $^2J_{PC}$=7.5 Hz, O—$CH_2$); 115.67–164.75 (aromatic C) ppm.

$^{31}$P-NMR spectrum ($CDCl_3$): 37.4 ppm.

$^{19}$F-NMR spectrum ($CDCl_3$): −105.7 (m) ppm.

3.2 Isobutyl (2-diphenylphosphinophenyl) methylphosphinate 36.5 ml (18.3 mmol) of potassium diphenylphosphide solution in THF (manufacturer: Aldrich) are added dropwise at −5° C. to a solution of 4.00 g (17.4 mmol) of isobutyl 2-fluorophenylmethylphosphinate in 20.0 ml of THF. After stirring for 72 hours at 23° C., the mixture is hydrolyzed by adding 20 ml of degassed water and stirring for 15 min. After extraction with ethyl acetate and drying the organic phase over $Na_2SO_4$, the mixture is concentrated under reduced pressure. After recrystallization from boiling heptane/THF mixture (9:1), 3.87 g of isobutyl (2-diphenylphosphinophenyl)methylphosphinate are obtained in the form of a colorless solid having an m.p. of 124° C.

$^1$H-NMR spectrum ($CDCl_3$): 0.66 (d, $J_{HH}$=7.2 Hz, 3H, $CH_3$); 0.75 (d, $J_{HH}$=7.2 Hz, 3H, $CH_3$); 1.95 (d, $J_{PH}$=14.8 Hz, 3H, P—$CH_3$); 1.49 (septet, $J_{HH}$=7.2 Hz, CH-isobutyl); 3.04 (m, 1H, $H_a$—$OCH_2$); 3.62 (m, 1H, $H_b$—$OCH_2$); 7.15–8.25 (14H, aromatic H) ppm.

<sup>13</sup>C-NMR spectrum (CDCl₃): 17.63 (dd, $^1J_{PC}$=100.3 Hz, $^4J_{PC}$=14.9 Hz, P—CH₃), 18.72 (d, $^4J_{PC}$=16.0 Hz, 2 CH₃); 28.91 (d, $^3J_{PC}$=6.5 Hz, CH-isobutyl); 70.48 (d, $^2J_{PC}$=6.5 Hz, O—CH₂); 128.31–140.46 (aromatic C) ppm.

$^{31}$P-NMR spectrum (CDCl₃): 42.5 (phosphinate P); –4.1 (phosphine P) ppm.

3.3 (2-Diphenylphosphinophenyl)methylphosphinic acid 0.30 g (7.6 mmol) of NaOH in 5 ml of water are added dropwise at 23° C. to a solution of 1.50 g (3.8 mmol) of isobutyl (2-diphenylphosphinophenyl)methylphosphinate in 5 ml of THF. After refluxing for 6 hours, the mixture is diluted with a further 5 ml of THF, 3.0 ml of 2N hydrochloric acid are added dropwise at 23° C. and the mixture is stirred for 20 min at 23° C. After phase separation, the aqueous phase is extracted twice, each time with 20 ml of dichloromethane, and the combined organic phases are washed with 20 ml of water. After drying over Na₂SO₄, complete evaporation under reduced pressure and drying in high vacuum, 1.17 g of (2-diphenylphosphinophenyl)methylphosphinic acid (92% of theory) are obtained in the form of a pale yellow solid having an m.p. of 167° C.

$^1$H-NMR spectrum (CDCl₃): 1.79 (d, $^2J_{PH}$=15.02 Hz, 3H, P—CH₃); 7.18–8.44 (14 H, aromatic H) ppm.

$^{13}$C-NMR spectrum (CDCl₃): 18.77 (dd, $^1J_{PC}$=100.0 HZ, $^4J_{PC}$=13.1 Hz, P—CH₃); 128.59–137.29 (aromatic C) ppm.

$^{31}$P-NMR spectrum (CDCl₃): 45.3 (d, $^3J_{PP}$=4.8 Hz, phosphinic acid P); –10.9 (d, $^3J_{PP}$=4.8 Hz, phosphine P) ppm.

EXAMPLE 4

4-Diphenylphosphinophenylphosphonic Acid 4.1 Diethyl 4-diphenylphosphinophenylphosphonate 25.8 ml (12.9 mmol) of potassium diphenylphosphide solution in THF (manufacturer: Aldrich) are added dropwise at –5° C. to a solution of 3.09 g (13.2 mmol) of diethyl 4-fluorophenylphosphonate, prepared as described in Phosphorus Sulfur 1980, 9(2), 197.202, in 20.0 ml of THF. After stirring for 19 hours at 23° C., the mixture is hydrolyzed by adding 20 ml of degassed water and stirring for 15 min. After extraction with ethyl acetate, and drying the organic phase over Na₂SO₄, the mixture is concentrated on a rotary evaporator. 4.20 g of diethyl 4-diphenylphosphinophenylphosphonate (82% of theory) are obtained in the form of a pale yellow oil.

$^1$H-NMR spectrum (CDCl₃): 1.30 (m, 6H, 2CH₃); 4.09 (m, 4H, 2 OCH₂); 7.06–7.80 (14H, aromatic H) ppm.

$^{31}$P-NMR spectrum (CDCl₃): 19.1 (phosphonate P); –4.0 (phosphine P) ppm.

4.2 4-Diphenylphosphinophenylphosphonic acid 0.40 g (10.0 mmol) of NaOH in 7 ml of water are added dropwise at 23° C. to a solution of 2.00 g (5.0 mmol) of diethyl 4-diphenylphosphinophenylphosphonate in 7 ml of THF. After refluxing for 6 hours, the mixture is diluted with a further 7 ml of THF, 4.0 ml of 2N hydrochloric acid are added dropwise at 23° C. and the mixture is stirred for 20 min at 23° C. After phase separation, the aqueous phase is extracted twice, each time with 25 ml of dichloromethane, and the combined organic phases are washed with 25 ml of water. After drying over Na₂SO₄, complete evaporation on a rotary evaporator and drying under reduced pressure, 1.54 g of 4-diphenylphosphinophenylphosphonic acid (90% of theory) are obtained in the form of a pale yellow solid having an m.p. of 87° C.

$^{31}$P-NMR spectrum (CDCl₃): 16.9 (s, phosphonic acid P); –11.1 (s, phosphine P) ppm.

EXAMPLE 5

Cross-coupling of 2-Chlorobenzonitrile with 4-Tolueneboronic Acid

To prepare the catalyst, 38.8 mg (0.219 mmol) of palladium(II) chloride and 54.0 mg (0.657 mmol) of sodium acetate in 2.4 ml of DMSO are stirred at 23° C. for 30 min under an argon atmosphere. 1.99 ml (0.875 mmol) of a 0.44 molar aqueous solution of sodium 4-diphenylphosphinophenylphosphinate, prepared as described in Example 1.4, are then added and the suspension is stirred for a further 30 min at 23° C. 30.0 g (0.2181 mol) of 2-chlorobenzonitrile, 32.6 g (0.240 mol) of 4-tolueneboronic acid and 16.2 g (70 mol %) of sodium carbonate are stirred into 120 ml of ethylene glycol under an argon atmosphere. 20 ml of water are added and the mixture is heated to 80° C. The above-described catalyst suspension is then added and the mixture is refluxed for 5 hours.

100 ml of ethyl acetate are added to the mixture at 23° C. The organic phase is separated off, concentrated on a rotary evaporator and fractionally distilled under reduced pressure. 31.6 g (75% of theory) of 2-cyano-4'-methylbiphenyl (b.p. 140° C./1.0 mbar; m.p. 50° C.) are obtained.

We claim:

1. A compound of the formula (I)

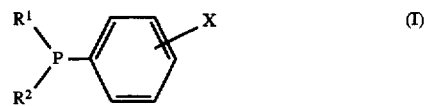

in which

X is a group of the formula (Ia)

in which

Z is hydrogen, an alkali metal, the stoichiometric equivalent of an alkaline earth metal, an ammonium ion, a mono-, di-, tri- or tetraalkylammonium or a radical $R^4$, where $R^4$ is a $C_1$–$C_{30}$-alkyl radical; and $R^3$ is a linear or branched $C_1$–$C_4$-alkyl radical;

$R^1$ and $R^2$ are identical or different and are each a linear, branched or cyclic $C_1$–$C_{30}$-alkyl radical or $C_6$–$C_{10}$-aryl radical which is unsubstituted or mono-substituted to penta-substituted by $C_1$–$C_3$-alkyl radicals, or $R^1$ and $R^2$ together with the trivalent P atom form a dibenzophospholyl of the formula

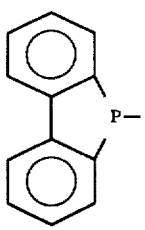

or a 3,4-dimethylphospholyl of the formula

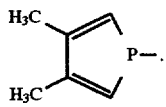

2. The compound as claimed in claim 1, wherein Z is $H^+$, $Na^+$, $K^+$, $Mg^{2+}/2$, $Ca^{2+}/2$, $NH_4^+$, mono-, di-, tri- or tetra-$(C_1-C_4)$-alkylammonium, methyl, ethyl, n-propyl, isopropyl, n-butyl, isobutyl or tert-butyl;

$R^3$ is methyl or ethyl; and $R^1$ and $R^2$ independently of one another are each methyl, cyclohexyl or phenyl.

3. The compound as claimed in claim 1, wherein the compound of the formula (I) is the free acid, the sodium salt or the isobutyl ester of (4-diphenylphosphinophenyl) methylphosphinic acid, of (3-diphenylphosphinophenyl) methylphosphinic acid or of (2-diphenylphosphinophenyl) methylphosphinic acid.

4. The compound as claimed in claim 2, wherein Z is isobutyl.

5. Sodium (4-diphenylphosphinophenyl) methylphosphinate.

6. A catalyst constituent in transition-metal-complex-catalyzed C—C linking reactions comprising at least one of said compounds claimed in claim 1.

* * * * *